United States Patent [19]

Pasqualini et al.

[11] Patent Number: 5,288,476
[45] Date of Patent: Feb. 22, 1994

[54] RADIOPHARMACEUTICAL PRODUCT MORE PARTICULARLY HAVING A CARDIAC TROPISM INCORPORATING A NITRIDE COMPLEX OF A TRANSITION METAL AND ITS PREPARATION PROCESS

[75] Inventors: Roberto Pasqualini, Clanart, France; Luciano Magon, Padova, Italy; André Bardy, Morangis, France; Adriano Duatti, Chiesuol Fosso, France; Andrea Marchi, Ferrara, Italy

[73] Assignee: CIS Bio International, Saclay, France

[21] Appl. No.: 675,938
[22] PCT Filed: Nov. 24, 1989
[86] PCT No.: PCT/FR89/00608
§ 371 Date: May 10, 1991
§ 102(e) Date: May 10, 1991
[87] PCT Pub. No.: WO90/06137
PCT Pub. Date: Jun. 14, 1990

[30] Foreign Application Priority Data

Jun. 12, 1989 [FR] France .............. 89 07731
Nov. 25, 1989 [FR] France .............. 88 15415

[51] Int. Cl.$^5$ .............. A61K 49/02; A61K 43/00
[52] U.S. Cl. .............. 424/1.65; 534/10; 534/14
[58] Field of Search .............. 424/1.1, 9; 534/10, 534/14

[56] References Cited

U.S. PATENT DOCUMENTS 4,923,969  5/1990  Bonnyman et al. .............. 534/14
4,925,925  5/1990  Deutsch .............. 534/10

FOREIGN PATENT DOCUMENTS 0007676  7/1979  European Pat. Off. .
WO8503063  7/1985  World Int. Prop. O. .

OTHER PUBLICATIONS

L. Kaden, et al.; "Nitrido complexes of technetium (V)", & Isotopenprasix 1981, 17(4), 174-5 Chemical Abstracts, vol. 95, No. 2, Jul. 13, 1981, p. 716, resume No. 17322r, Columbus, Ohio.

J. Baldas, et al.; "The preparation, characterization and reactions of chlorotetrakis(thiourea)-nitridotechnetium(V) chloride", & Inorg. Chim. Acta 1988, 141(2), 153-4, Chemical Abstracts, vol. 108, No. 22, May 30, 1988, p. 712, resume No. 197162g, Columbus. Ohio.

International Journal of Radiation/Applications & Instrumentation Paret A. vol. 38, No. 8, 1987, GB pp. 665–668; Ballinger, J. R.: "Technetium-99m Diethyldithiocarbamate (DDC): Comparison with Thallium-201DDC as an Agent for Brain Imaging".

International Journal of Applied Radiation and Isotopes, vol. 36, No. 2, Feb. 1985, Oxford, GB, pp. 133–139, Baldas J. et al.: "Substitution reactions of 99m TcNCl4-A. Route to a new class of 99m Tc-Radiopharmaceuticals".

Primary Examiner—Gary Geist
Attorney, Agent, or Firm—Oblon, Spivak, McClelland, Maier & Neustadt

[57] ABSTRACT

The invention relates to a radiopharmaceutical product more particularly having a cardiac tropism, incorporating a nitride complex of a transition metal and the process for the preparation thereof.

This complex complies with the formula:

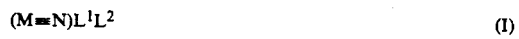

in which M is a transition metal, e.g. Tc99m, Re 186 or Re 188 and L1 and L2, which can be the same or different, comply with the formula:

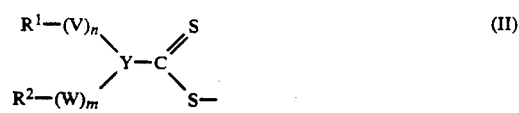

in which $R^1$ and $R^2$ can be alkyl radicals, V and W can be O, S or Se, n=0 or 1, m=0 or 1, and Y represents N, P or As.

23 Claims, No Drawings

RADIOPHARMACEUTICAL PRODUCT MORE PARTICULARLY HAVING A CARDIAC TROPISM INCORPORATING A NITRIDE COMPLEX OF A TRANSITION METAL AND ITS PREPARATION PROCESS

The present invention relates to a radiopharmaceutical product or radioactive drug in particular having a cardiac tropism, which comprises a nitride complex of a transition metal having a part M≡N, in which M represents the transition metal. It more particularly applies to radiopharmaceutical products having a cardiac tropism.

It is pointed out that the term transition metal means a metal whose coating d is partly filled in the standard oxidation degree of said metal. They are elements in periods III to XII of the periodic table of elements consisting of eighteen columns Examples of such metals are Tc, Ru, Co, Pt, Fe, Os, Ir, W, Re, Cr, Mo, Mn, Ni, Rh, Pd, Nb and Ta.

Technetium nitride complexes have been described by J. Baldas et al in the following documents: International Patent Application WO85/03063, J. Chem. Soc. Dalton Trans., 1981, pp. 1798-1801 and in the book "Technetium in Chemistry and Nuclear Medicine", M. Nicolini, G. Bandoli and U. Mazzi, Cortine Int. Verona, 1986, pp. 103 to 108.

These documents describe the preparation of technetium nitride complexes by a substitution reaction on $^{99m}TcNCl_4$ and it is stated that these complexes can be used as radiopharmaceutical products. However, these documents fail to provide any results giving evidence regarding the fixing of the complexes in the body and consequently give no indication of their tropisms with respect to certain organs and in particular the heart.

Among the radiopharmaceutical products having a cardiac tropism, technetium complexes are known, which contain as the ligand isonitriles substituted by an ether, in the manner described in European patent application EP-A-0 233 368 and dioxime-based technetium complexes as described in European patent EP-A-0 268 801. These complexes are formed from ligands which are difficult to synthesize.

Thus, research has been carried out to find other radio-pharmaceutical products having satisfactory properties for use as diagnosis or therapy products and more particularly radiopharmaceutical products with a cardiac tropism, e.g. for myocardial scintigraphy.

The present invention specifically relates to a radiopharmaceutical product, which comprises a complex of a transition metal complying with the formula:

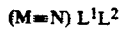

in which M is a transition metal and $L^1$ and $L^2$, which can be the same or different, comply with the formula:

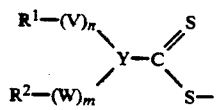

in which V and W, which can be the same or different, represent O, S or Se, n and m, which can be the same or different, are equal to 0 or to 1, Y represents N, P or As, and $R^1$ and $R^2$, which can be the same or different, represent a straight or branched alkyl radical with 1 to 10 carbon atoms, which is either not substituted or substituted by $-O-R^3$, $OOC-R^3$, $OCNR^4R^5$ or $-NR^4R^5$ groups, in which $R^3$ is a straight or branched alkyl radical with 1 to 5 carbon atoms and $R^4$ and $R^5$, which can be the same or different, are hydrogen atoms or straight or branched alkyl radicals with 1 to 5 carbon atoms, or in which $R^1$ and $R^2$ together form a hydrocarbon cycle optionally containing one or more heteroatoms.

The radiopharmaceutical products incorporating transition metal complexes in accordance with the above formula in particular have a cardiac tropism, which makes them interesting as heart therapy or diagnosis products.

In the radiopharmaceutical products according to the invention, the transition metal nitride complex can be of different types.

Thus, according to a first embodiment of the invention, in the aforementioned formula, Y represents N, m and n are equal to O, $L^1$ and $L^2$ are identical and $R^1$ and $R^2$ are unsubstituted alkyl radicals.

In this first embodiment according to the invention, $R^1$ and $R^2$ are preferably also identical.

For example, $L^1$ and $L^2$ can be in accordance with the following formulas:

According to a second embodiment of the invention, Y represents N, m and n are equal to 0, $L^1$ and $L^2$ are identical and at least one of the $R^1$ and $R^2$ represents an alkoxy alkyl radical.

For example, $L^1$ and $L^2$ can comply with the following formulas:

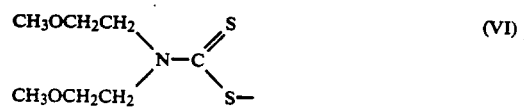

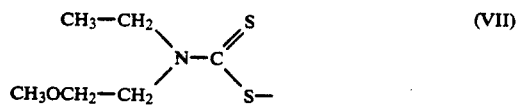

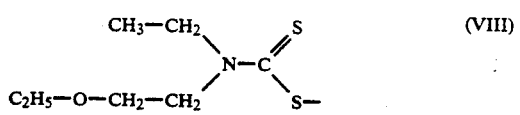

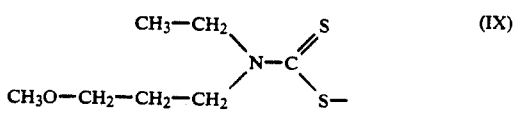

According to a third embodiment of the invention, the transition metal complex is in accordance with the formula:

in which M is a transition metal and $L^1$ and $L^2$ comply with the formula:

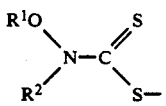

in which $R^1$ and $R^2$ have the meanings given in claim 1.

Examples of such complexes are those for which $R^1$ represents $CH_3$ and $R^2$ represents $CH_3$— or $CH_3$—$CH_2$—, or for which $R^1$ represents $CH_3$—$CH_2$— and $R^2$ represents $CH_3$— or $CH_3$—$CH_2$—.

In the complexes according to the invention, the transition metal used more particularly depends on the application of the radiopharmaceutical product. Thus, when it is wished to use the product for diagnosis, use is made of a radioactive transition metal with a relatively short period, e.g. technetium $^{99m}$.

In the case where it is wished to use the radiopharmaceutical product for therapy, use is made of a transition metal emitting an effective radiation for the therapy and which has a longer life, such as rhenium, e.g. Re-186 or Re-188.

The technetium nitride complexes used in the invention can be prepared by the Baldas process. However, preference is generally given to the preparation thereof by a simpler process, which is easier to carry out in a hospital department and which leads to high yields.

This process comprises the following successive stages: $1^0$) reacting an oxygenated compound of a transition metal M with:

a) a first ligand chosen from within the group of substituted or unsubstituted, aromatic and aliphatic phosphines and polyphosphines and b) a second reagent chosen from among the ammonium and alkali metal nitrides and the nitrogenous ligands having a $>$N—N$<$ in which the N are connected to hydrogen atoms and/or to monovalent organic groups via a carbon atom, or in which one of the N is connected to the carbon atom of a divalent organic group via a double bond and the other N is connected to hydrogen atoms and/or monovalent organic groups via a carbon atom and $2^0$) reacting the intermediate obtained in the first stage with a compound in accordance with the formula:

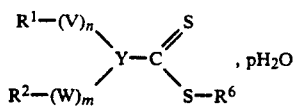

in which $R^1$, $R^2$, V, W, n, m and Y have the meanings given hereinbefore, $R^6$ is an alkali metal ion, $H^+$ or $NH_4^+$ and p is equal to 0 or an integer between 1 and 5.

When the process is performed using technetium as the transition metal, the oxygenated compound of the transition metal can be ammonium or alkali metal pertechnetate. In the case where the transition metal is rhenium, it is possible to use an ammonium or alkali metal perrhenate.

Thus, in the first stage of the process, preparation takes place of a technetium nitride complex, which is then reacted with the compound of formula (X) in order to exchange the first and second ligands by this compound.

In order to carry out the reaction, it is possible to aseptically introduce the first ligand and namely either the ammonium or alkali metal nitride, or the nitrogenous ligand, into a container and then add the requisite quantity of the oxygenated transition metal compound, e.g. technetium $^{99m}$ pertechnetate, after adjusting the pH to an appropriate value by the addition of acid or base. It is then possible to carry out the reaction at ambient temperature or at a higher temperature between 50° and 100° C. The temperature and pH used in particular depend on the second nitrogenous ligand. Operation generally takes place between pH2 and 7.

In the first stage, it is possible to use the first and second ligands in the form of alcoholic, hydroalcoholic or aqueous solutions and simply add these solutions to the oxygenated compound of the transition metal.

In the second stage, the product obtained in the first stage is reacted with the compound of formula (X) in aqueous solution, generally at a pH above 7 and e.g. in a sodium bicarbonate-carbonate buffer.

In this second stage, it is also possible to use an alcoholic or hydroalcoholic solution of compound (X).

The first ligand making it possible to obtain the formation of a nitride complex is an organic ligand with an electron donor phosphorus atom chosen from among substituted or unsubstituted, aliphatic and aromatic phosphines and polyphosphines.

The phosphines which can be used can comply with the formula:

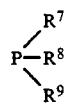

in which $R^7$, $R^8$ and $R^9$, which can be the same or different, represent a hydrogen atom, an alkyl radical, an aryl radical, an alkoxy radical or an alkyl or aryl radical substituted by a group chosen from among the amino, amido, cyano and sulphonate radicals.

Examples of phosphines of this type are triphenyl phosphine, trisulphonated triphenyl phosphine, diethyl phenyl phosphine, triethyl phosphine, trimethyl phosphine and tris(2-cyanoethyl)-phosphine $P(CH_2—CH_2CN)_3$.

In the first stage, it is possible to use as the second reagent either an ammonium or alkali metal nitride, e.g. sodium nitride, or a nitrogenous ligand having the $>$N—N$<$, as in hydrazine and its derivatives. It is possible to use numerous nitrogenous ligands of this type. Generally, preference is given to the use as the nitrogenous ligand of dithiocarbazic acid or a derivative thereof.

Thus, the second nitrogenous ligand can be dithiocarbazic acid or a derivative thereof in accordance with the formula:

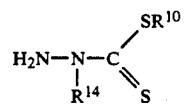

in which $R^{10}$ represents a hydrogen atom, an alkyl radical or an aryl radical and $R^{14}$ represents a hydrogen atom, an alkyl radical, an aryl radical, an alkoxy radical, an alkyl radical substituted by at least one group chosen from among the hydroxy, carboxy, amino, amido and mercapto radicals, or an aryl radical substituted by at least one group chosen from among the halogen atoms and the alkoxy, hydroxy, amino and mercapto radicals and the amino radicals substituted by at least one alkyl radical.

It can also be a condensation product obtained by the reaction of dithiocarbazic acid with a ketone or aliphatic aldehyde of formula $R^{15}$—CO—$R^{16}$. In this case, it complies with the formula:

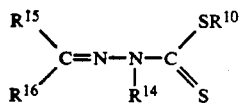

in which $R^{10}$ represents a hydrogen atom, an alkyl radical or an aryl radical; $R^{14}$ represents a hydrogen atom, an alkyl radical, an aryl radical, an alkoxy radical, an alkyl radical substituted by at least one group chosen from among the hydroxy, carboxy, amino, amido and mercapto radicals, or an aryl radical substituted by at least one group chosen from among the halogen atoms and alkoxy, hydroxy, amino and mercapto radicals or amino radical substituted by at least one alkyl radical; and $R^{15}$ and $R^{16}$, which can be the same or different, represent a hydrogen atom, an alkyl radical or an alkyl radical substituted by at least one group chosen from among the hydroxy, carboxy, amino, amido and mercapto radicals.

The dithiocarbazic acid derivative used as the second ligand can also be the condensation product of dithiocarbazic acid with a ketone or aromatic aldehyde. In this case, the derivative complies with the formula:

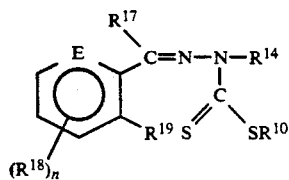

in which $R^{10}$ represents a hydrogen atoms, an alkyl radical or an aryl radical; $R^{14}$ represents a hydrogen atom, an alkyl radical, an aryl radical, an alkoxy radical, an alkyl radical substituted by at least one group chosen from among the hydroxy, carboxy, amino, amido and mercapto radicals or an aryl radical substituted by at least one group chosen from among the halogen atoms and the alkoxy, hydroxy, amino and mercapto radicals and the amino radical substituted by at least one alkyl radical; $R^{17}$ represents a hydrogen atom, an alkyl radical, an alkyl radical substituted by at least one group chosen from among the hydroxy, carboxy, amino, amido and mercapto radicals, $R^{18}$ represents a hydrogen atom, a halogen atom, an alkoxy radical, an amino radical or an amino radical substituted by at least one alkyl group, $R^{19}$ represnts a hydrogen atom, a hydroxy radical or a mercapto radical, E represents a carbon atom or a nitrogen atom and n is an integer between 1 and 4, on in which n is equal to 2 and the two $R^{18}$ are neighbouring hydrocarbon chains together forming an aromatic cycle.

It is also possible to use as the second ligand the product obtained by the condensation of dithiocarbazic acid with a ketone having a 5-link heterocycle. In this case, the second ligand complies with the formula:

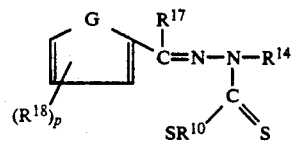

in which $R^{10}$ represents a hydrogen atom, an alkyl radical or an aryl radical; $R^{14}$ represents a hydrogen atom, an alkyl radical, an aryl radical, an alkoxy radical, an alkyl radical substituted by at least one group chosen from among the hydroxy, carboxy, amino, amido and mercapto radicals, or an aryl radical substituted by at least one group chosen from among the halogen atoms and the alkoxy, hydroxy, amino and mercapto radicals and the amino radical substituted by at least one alkyl radical; $R^{17}$ represents a hydrogen atom, an alkyl radical, an alkyl radical substituted by at least one group chosen from among the hydroxy, carboxy, amino, amido and mercapto radicals, $R^{18}$ represents a hydrogen atom, a halogen atom, an alkoxy radical, an amino radical or an amino radical substituted by at least one alkyl group, G is S or O, and p is 1, 2 or 3.

Examples of second nitrogenous ligands which can be used are S-methyl-beta-N(2-hydroxyphenyl)methylene dithiocarbazate, S-methyldithiocarbazate, S-methyl-N-methyl-dithiocarbazate, alpha-N-methyl-S-methyl-beta-N-pyridylmethylene dithiocarbazate, and alpha-N-methyl-S-methyl-beta-N(2-hydroxyphenyl)methylene dithiocarbazate.

When the radiopharmaceutical product according to the invention is for use in diagnosis, it is generally necessary to prepare it at the moment of use.

The invention also relates to a kit for the preparation of a radiopharmaceutical product with cardiac tropism and which comprises a first bottle containing a phosphine, a second bottle containing sodium nitride, dithiocarbazic acid or a derivative thereof and a third bottle containing a compound complying with the formula:

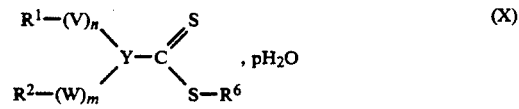

in which $R^1$, $R^2$, V, W, n, m and Y have the meanings given hereinbefore, $R^6$ is an alkali metal ion, $H^+$ or $NH_4^+$ and p is equal to 0 or is an integer from 1 to 5.

This kit makes it possible to directly prepare the desired radiopharmaceutical product in a nuclear medicine hospital department by mixing the content of the first two bottles with a solution of the oxygenated transition metal solution, e.g. an ammonium or alkali metal pertechnetate solution, followed by the addition to the thus obtained product of the content of the third bottle.

The products respectively present in the first, second and third bottles can be in liquid or lyophilized form.

In certain cases, it is also possible to mix the content of the first two bottles prior to use. In this case, the kit will only have a first bottle containing a phosphine and the second reagent constituted either by sodium nitride or by dithiocarboxylic acid or a derivative thereof, and a second bottle containing the compound of the aforementioned formula (VII).

In view of the fact that the products are intended for intravenous injection in living beings, it is necessary to use appropriate production and use conditions for obtaining appropriately sterile and apyrogenic solutions.

In order to prepare the solutions, it is possible to use sterile and apyrogenic water or sterile and apyrogenic alcoholic or hydroalcoholic solutions and store the solutions under nitrogen.

In order to prepare the lyophilized compositions, solutions obtained under the conditions described hereinbefore are lyophilized in standard equipment.

The radiopharmaceutical products according to the invention can be more particularly used in myocardial scintigraphy. In this case, following the preparation of the technetium nitride complex, the latter is injected into the patient to be examined and the heart is then examined by scintigraphy.

For the injection of the product, the quantities of the different ligands are such that they substantially correspond to the stoichiometry of the complexes to be obtained. The final quantity injected is in particular dependent on the ligands used and their toxicity.

Generally, satisfactory results are obtained by using total ligand quantities of 0.05 to 0.40 mg/kg of body weight.

The total transition metal, e.g. technetium dose is generally 185 to 740 Mbq (5 to 20 millicuries).

Following the administration of the transition metal nitride complex, it is possible to carry out a satisfactory examination within 0.5 to 3 h obtaining a good contrast, clear images and a good detection of lesions.

Other characteristics and advantages of the invention can be gathered from the following illustrative, non-limitative examples.

EXAMPLE 1

Preparation of the bis(diethyl dithiocarbamate) nitride complex $^{99m}Tc(V)(TcNDEDC)$ a) Preparation of the intermediate Into a penicillin-type bottle are introduced 0.4 ml of a solution containing $2 \cdot 10^{-2}$ mole/l (2.5 mg/ml) of S-methyl dithiocarbazate in ethyl alcohol, then 0.2 ml of a $2 \cdot 10^{-2}$ mole/l (5 mg/ml) triphenyl phosphine solution in ethyl alcohol and 0.1 ml of 1N hydrochloric acid. This is followed by the addition of 0.5 to 1 ml of a sodium pertechnetate ($Tc^{99m}$) solution and the reaction is carried out at 80° C. for 30 minutes or at 100° C. for 15 minutes.

b) Preparation of the final complex

To the content of the bottle obtained in stage a) are added 0.1 ml of 1N NaOH solution and 0.5 ml of a solution containing 0.18 mole/l of trihydrated sodium diethyl dithiocarbamate (40 mg/ml) in a 0.5 mol/l$^{-1}$ sodium bicarbonate-carbonate buffer at pH 9.0.

The reaction is carried out for 15 minutes at 100° C., 30 minutes at 80° C. or 60 minutes at ambient temperature.

The radiochemical purity of the complex obtained is tested by carrying out thin film chromatography using a silica gel and toluene as the solvent. The complex obtained has a Rf of 0.3 to 0.4. The radio-chemical purity is equal to or greater than 93%.

EXAMPLE 2

Preparation of the bis(diethyl dithiocarbamate) nitride complex $^{99m}Tc(V)$ (TcNDEDC)

a) Preparation of the intermediate

Into a penicillin-type bottle are introduced 0.2 ml of a solution containing $7.7 \cdot 10^{-2}$ mole/l (5.0 mg/ml) of sodium nitride in water, then 0.2 ml of a $2 \cdot 10^{-2}$ mole/l (5 mg/ml) triphenyl phosphine solution in ethyl alcohol and 0.1 ml of 1N hydrochloric acid. This is followed by the addition of 0.5 to 1 ml of a sodium pertechnetate solution (Tc-99m) and the reaction is performed at 80° C. for 30 minutes or at 100° C. for 15 minutes.

b) Preparation of the end product

To the content of the bottle obtained in stage a) are added, as in example 1, 0.1 ml of a 1N NaOH solution and 0.5 ml of a solution containing 0.18 mole/l (40 mg/ml) of trihydrated sodium diethyl dithiocarbamate in a 0.5 mole/l sodium bicarbonate-carbonate buffer and at pH 9. The reaction is carried out as in example 1.

Testing also takes place of the radiochemical purity of the product by thin film chromatography and the results are identical to those of example 1.

EXAMPLE 3

Preparation of the bis(diethyl dithiocarbamate) nitride complex $^{99m}Tc(V)$ (TcNDEDC)

a) Preparation of the intermediate

Into a penicillin-type bottle are introduced 0.2 ml of a solution containing $7.7 \cdot 10^{-2}$ mole/l (2 mg/ml) of sodium nitride in water, then 0.4 ml of a solution containing $1 \cdot 10^{-2}$ mole/l (2 mg/ml) of tris(2-cyanoethyl)-phosphine in water and 0.1 ml of 1N hydrochloric acid.

This is followed by the addition of 0.5 to 5 ml of a sodium pertechnetate ($^{99m}Tc$) solution and the reaction is performed at 80° C. for 30 minutes or at 100° C. for 15 minutes-preparation without alcohol.

b) Preparation of the final complex

The same operating procedure as in example 1, paragraph b) is followed for the preparation of the TcNDEDC complex from the previously obtained intermediate.

EXAMPLE 4

Preparation of the bis(diethyl dithiocarbamate) nitride complex $^{99m}Tc(V)$ (TcNDEDC)

a) Preparation of the intermediate

Into a penicillin-type bottle are introduced 0.2 ml of a solution containing $7.7 \cdot 10^{-2}$ mole/l (5 mg/ml) of sodium nitride in water, then 0.4 ml of a solution containing $1 \cdot 10^{-2}$ mole/l of tris(2-cyanoethyl)phosphine.

This is followed by the addition of 0.5 to 5 ml of a sodium pertechnetate ($^{99m}Tc$) solution and the reaction is performed at 80° C. for 30 minutes or 100° C. for 15 minutes. This operation is carried out at a pH close to 7.

b) Preparation of the end product

To the content of the bottle obtained in stage a) are added 0.5 ml of a solution containing 0.18 mole/l (40 mg/ml) of trihydrated sodium diethyl dithiocarbamate in a 0.5 mole/l sodium bicarbonate-carbonate buffer and at pH 9. The reaction is carried out as in example 1.

EXAMPLE 5

Preparation of the bis(dimethyl dithiocarbamate) nitride complex $^{99m}$Tc(V) (TcNDMDC)

The same operating procedure as in example 1 is followed, whilst in the final stage the diethyl dithiocarbamate is replaced by 0.5 ml of a solution containing 0.18 mole/l of dihydrated sodium dimethyl dithiocarbamate (30 mg/ml) in the same buffer. This gives the technetium complex TcNDMDC with a radiochemical purity equivalent to that of example 1.

EXAMPLE 6

Preparation of the bis(di-n-propyl dithiocarbamate) nitride complex $^{99m}$Tc(V) (TcNDPDC)

The same operating procedure as in example 1 is followed, but the diethyl dithiocarbamate is replaced by 0.5 ml of a solution containing 0.18 mole/l (40.7 mg/ml) of sesquihydrated sodium di-n-propyl dithiocarbamate in a mixture of the 0.5 mole/l sodium bicarbonate-carbonate buffer and at pH 9 and ethyl alcohol in a volume ratio of 7:3.

This gives the technetium complex TcNDPDC having a radiochemical purity equivalent to that of example 1.

EXAMPLES 7 TO 9

In these examples testing takes place of the properties of the complexes obtained in examples 1, 5 and 6, by determining their bio distribution in male rats of the Sprague Dawley strain weighing 200±20 g.

In this case, into the rats, anesthetized with sodium pentobarbital, is injected a dose corresponding to 15 μmole/kg of body weight of myotropic ligand, which corresponds to a radiation dose of 1 to 2.5 μCi. 5, 30 or 60 minutes following the injection of the product, the rats are sacrificed and their organs removed. This is followed by the determination of the radioactivity present in each of the organs.

The results obtained are given in the following table 1 and expressed as a percentage of the injected radioactivity found in the organs, following sampling and counting.

The values given in each box in the table represent the mean value and the two extreme values.

This table makes it clear that these complexes have a good cardiac tropism.

EXAMPLE 10

Preparation of the bis(N,N-dimethoxydiethyl dithiocarbamate) nitride complex $^{99m}$Tc(V) (TcNMEDC)

a) Preparation of the intermediate

Into a penicillin-type bottle are introduced 0.5 ml of a solution containing $0.8 \cdot 10^{-2}$ mole/l (1 mg/ml) of S-methyl-N-methyl dithiocarbazate in water, then 0.5 ml of a $2 \cdot 10^{-2}$ mole/l (10 mg/ml) trisulphonated triphenyl phosphine solution in water and 0.1 ml of 1N hydrochloric acid. This is followed by the addition of 0.5 to 5 ml of a sodium pertechnetate (Tc$^{99m}$) solution and the reaction is carried out at 80° C. for 30 minutes or at 100° C. for 15 minutes.

b) Preparation of the final complex

To the content of the bottle obtained in stage a) are added 0.1 ml of 1N NaOH solution and 0.5 ml of a solution containing 0.1 mole/l of sodium dimethoxyethyl dithiocarbamate (23 mg/ml) in a 0.5 mole/l sodium bicarbonate-carbonate buffer at pH 9.5. The reaction is carried out for 30 minutes at ambient temperature.

This gives the nitride complex TcNMEDC or the complex of formula (Tc≡N)L$^1$L$^2$ with L$^1$ and L$^2$ representing the compound of formula (VI).

EXAMPLE 11

Preparation of the bis(N-ethyl-N-(2-methoxyethyl)dithiocarbamate) nitride complex $^{99m}$Tc(V) (TcNEMEC)

The same operating procedure as in example 10 is followed for the preparation of the intermediate from S-methyl-N-methyl dithiocarbazate and trisulphonated triphenyl phosphine. This is followed by the preparation of the end product by adopting the operating procedure of example 10, but using 0.5 ml of a 0.1 mole/l solution of sodium N-ethyl-N-(2-methoxyethyl)-dithiocarbamate (20 mg/ml) in place of the sodium dimethoxyethyl dithiocarbamate of example 10.

This gives the bis(N-ethyl-N-(2-methoxyethyl)-dithiocarbamate nitride complex $^{99m}$Tc(V), i.e. the product of formula:

$$(Tc\equiv N)L^1L^2$$

TABLE 1

| | TcNDMDC (CH$_3$)$_2$N−C(=S)(S−) | | | TcNDEDC (C$_2$H$_5$)$_2$N−C(=S)(S−) | | | TNDPDC (C$_3$H$_7$)$_2$−N−C(=S)(S−) | | |
|---|---|---|---|---|---|---|---|---|---|
| | number of animals: 3 | | | number of animals: 5 | | | number of animals: 5 | | |
| whole organs | Time between I.V. injection and sacrifice | | | | | | | | |
| | 5 min | 30 min | 60 min | 5 min | 30 min | 60 min | 5 min | 30 min | 60 min |
| Liver | 17.5 | 18.2 | 27.5 | 20.2 | 24.1 | 25 | 27.2 | 33.2 | 28.5 |
| | 16.6–18.1 | 16.7–20.0 | 27.6–28.5 | 14.9–22.1 | 23.2–26.1 | 24.3–26.1 | 23.1–32.3 | 29.8–35.2 | 22.3–33.4 |
| Kidneys | 5.2 | 1.9 | 1.8 | 4.9 | 3.5 | 3.0 | 2.9 | 2.6 | 2.1 |
| | 5.1–5.3 | 1.8–2.1 | 1.7–2.2 | 4.6–5.2 | 3.2–4.1 | 2.8–3.2 | 2.4–3.6 | 2.0–3.3 | 1.6–2.6 |
| Lungs | 4.4 | 6.0 | 6.5 | 9.2 | 1.8 | 1.2 | 2.6 | 1.1 | 0.6 |
| | 3.9–4.6 | 4.5–7.5 | 4.5–11.5 | 8.5–9.5 | 1.6–1.9 | 1.3–1.4 | 2.1–3.4 | 1.0–1.3 | 0.4–0.9 |
| Brain | 0.52 | 0.18 | 0.15 | 0.7 | 0.2 | 0.1 | 0.2 | 0.2 | 0.2 |
| | 0.48–0.58 | 0.17–0.19 | 0.14–0.16 | 0.7–0.7 | 0.2–0.2 | 0.1–0.1 | 0.1–0.2 | 0.2–0.2 | 0.1–0.2 |
| Heart | 2.3 | 0.70 | 0.60 | 2.6 | 1.6 | 1.4 | 1.8 | 1.5 | 1.3 |
| | 2.1–2.5 | 0.6–0.9 | 0.5–0.7 | 2.4–2.7 | 1.6–1.7 | 1.3–1.5 | 1.4–1.9 | 1.4–1.7 | 1.2–1.4 |
| Whole blood | 3.0 | 2.3 | 3.0 | 9.2 | 2.3 | 1.8 | 3.5 | 2.0 | 1.5 |
| | 2.9–3.2 | 2.0–2.5 | 2.9–3.2 | 7.5–10.1 | 1.8–3.0 | 1.6–2.2 | 2.5–4.6 | 1.8–2.5 | 1.0–1.9 | with $L^1$ and $L^2$ representing the compound of formula (VII).

EXAMPLE 12

Preparation of the bis(N-ethyl-N-(3-methoxypropyl)dithiocarbamate) nitride complex $^{99m}$Tc(V) (TcNEMPC)

The same operating procedure as in examples 10 and 11 is adopted for the preparation of this complex from the intermediate obtained in stage a) of example 10 and using as the reagent in stage b) 0.5 ml of a 0.1 mole/l solution of sodium N-ethyl-N-(3-methoxypropyl)-dithiocarbamate (22 mg/ml).

This gives the nitride complex TcNEMPC or the complex of formula $(Tc\equiv N)L^1L^2$ with $L^1$ and $L^2$ representing the compound of formula (VIII).

EXAMPLE 13

Preparation of the bis(N-ethyl-N-(2-ethoxyethyl)-dithiocarbamate) nitride complex $^{99m}$Tc(V) (TcNEEDC)

The same operating procedure as in example 10 is used for the preparation of the intermediate and the end product, except that the reagent used for the preparation of the end product is 0.5 ml of a 0.1 mole/l solution of sodium N-ethyl-N-(2-ethoxyethyl)-dithiocarbamate (22 mg/ml).

This gives the nitride complex TcNEEDC or the complex of formula $(Tc\equiv N)L^1L^2$ with $L^1$ and $L^2$ representing the compound of formula (IX).

EXAMPLE 14

Preparation of the bis(N-methoxy-N-methyl dithiocarbamate) nitride complex $^{99m}$Tc (TcNMEMC)

a) Preparation of the intermediate

The same operating procedure as in example 10 is used for preparing an intermediate, whilst using the same reagents and the same reaction conditions.

b) Preparation of the final complex

To the content of the bottle obtained in stage a) are added 0.1 ml of a 1N NaOH solution and 0.5 ml of a solution containing 0.13 mole/l of sodium N-methoxy-N-methyl dithiocarbamate (20 mg/ml) in a 0.5 mole/l sodium bicarbonate-carbonate buffer at pH 9.5. The reaction is performed for 30 minutes at ambient temperature.

This gives the complex TcNMEMC, namely that of formula $(Tc\equiv N)L^1L^2$ with $L^1$ and $L^2$ representing:

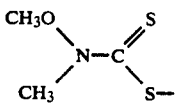

EXAMPLE 15

Preparation of bis(N-methoxy-N-ethyl dithiocarbamate) nitride complex $^{99m}$Tc(V) (TcNMEEC)

The same operating procedure as in example 14 is adopted for preparing this technetium complex from the same intermediate and using for the preparation of the end product 0.5 ml of a 0.12 mole/l sodium N-methoxy-N-ethyl dithiocarbamate solution (20 mg/ml). This gives the complex TcNMEEC, namely the complex of formula $(Tc\equiv N)L^1L^2$ with $L^1$ and $L^2$ representing the formula:

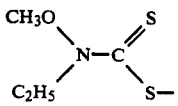

EXAMPLE 16

Preparation of bis(N-ethoxy-N-methyl dithiocarbamate) nitride complex $^{99m}$Tc(V) (TcNETMC)

This example adopts the operating procedure of example 14, except that the reagent used for preparing the end product is 0.5 ml of a 0.12 mole/l solution of sodium N-ethoxy-N-methyl dithiocarbamate (20 mg/ml).

This gives the technetium complex of formula $(Tc\equiv N)L^1L^2$ with $L^1$ and $L^2$ representing the formula:

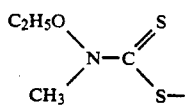

EXAMPLE 17

Preparation of the bis(N-ethoxy-N-ethyl dithiocarbamate) nitride complex $^{99m}$Tc(V) (TcNETEC)

The same operating procedure as in example 14 is followed for the preparation of this technetium complex using as the reagent in the second stage 0.5 ml of a solution containing 0.11 mole/l of sodium N-ethoxy-N-ethyl dithiocarbamate (20 mg/ml).

This gives the complex of formula $(Tc\equiv N)L^1L^2$ with $L^1$ and $L^2$ representing the formula:

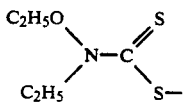

EXAMPLE 18

The biological properties of the complexes obtained in examples 10 to 13 and 17 are tested by determining the retention of the myocardium in dogs weighing between 10 and 15 kg.

In this case, into dogs anesthetized with sodium pentobarbital and kept under ventilation, is injected a dose corresponding to 2 μmole/kg of body weight of myotropic technetium complex, which corresponds to a 2 to 5 mCi radiation dose.

The retention of the radioactivity by the myocardium and the surrounding organs (lungs and liver) is determined by dynamic acquisition between injection and the end of the examination using a gamma camera and by defining areas of interest for each organ. All the tested complexes allow a good visual display of the myocardium.

The heart/liver and heart/lung contrast values are measured by performing a simple ratio between the number of beats per surface unit (or pixel) in the organs.

The heart/liver and heart/lung ratio values are given in table 2.

Therefore the target organ/background noise ratios are very favourable.

EXAMPLES 19 TO 21

These examples test the properties of the complexes obtained in examples 15 to 18 by determining their biodistribution in male rats of the Sprague Dawley strain weighing 200±20 g.

In this case, into rats, anesthetized with sodium pentobarbital, is injected a dose corresponding to 15 μmole/kg of body weight of myotropic ligand, which corresponds to a radiation dose of 1 to 2.5 μCi.

5, 30 or 60 minutes following the injection of the product, the rats are sacrificed and the organs removed. The radioactivity present in each of the organs is determined.

The results obtained are given in table 3 and expressed as a percentage of the injected radioactivity found in the organ, following sampling and counting. The values given in each box of the table represent the mean value and the two extreme values.

The table shows that these complexes have a good cardiac tropism.

TABLE 2

HEART/LIVER AND HEART/LUNG RATIOS FOR CERTAIN DITHIOCARBAMATE Tc≡N COMPLEXES $$L_1 = L_2 = \begin{array}{c} R^1 \\ \diagdown \\ / \\ R^2 \end{array} NCS_2$$

| Ex | $R^1$, $R^2$ | Ratios | 5 | 15 | 30 | t min 75 | 90 | 120 |
|---|---|---|---|---|---|---|---|---|
| 17 | $R^1 = C_2H_5-$ | Heart/liver | 2 01 | 1 39 | 1 24 | 0 90 | | 0 82 |
| | $R^2 = C_2H_5O-$ | Heart/lung | 1 10 | 1 33 | 1 61 | 1 75 | | 2 64 |
| 11 | $R^1 = C_2H_5-$ | Heart/liver | 1 44 | 1 02 | 0 86 | | 0 66 | |
| | $R^2 = CH_3O(CH_2)_2-$ | Heart/lung | 2 75 | 2 60 | 2 41 | | 1 66 | |
| 10 | $R^1 = CH_3O(CH_2)_2-$ | Heart/liver | 1 27 | 0 61 | 0 38 | | | |
| | $R^2 = CH_3O(CH_2)_2-$ | Heart/lung | 2 02 | 1 70 | 1 35 | | | |
| 13 | $R^1 = C_2H_5-$ | Heart/liver | 1 43 | 0 97 | 0 87 | 0 63 | 0 58 | 0 56 |
| | $R^2 = C_2H_5O(CH_2)_2-$ | Heart/lung | 1 36 | 1 66 | 1 68 | 3 10 | 2 97 | 2 46 |
| 12 | $R^1 = C_2H_5-$ | Heart/liver | 0 95 | 0 74 | 0 60 | 0 32 | 0 27 | 0 18 |
| | $R^2 = CH_3O(CH_2)_3-$ | Heart/lung | 1 39 | 2 16 | 2 44 | 2 04 | 1 87 | 1 54 |

TABLE 3

| | EX. 6 (TCNMEMC) $CH_3-O\diagdown N-CS_2 / CH_3$ | | | EX. 7 (TCNMEEC) $CH_3-O\diagdown N-CS_2 / C_2H_5$ | | |
|---|---|---|---|---|---|---|
| $L_1 = L_2$ whole organs | Time between I.V. injection and sacrifice | | | | | |
| | 5 min | 30 min | 60 min | 5 min | 30 min | 60 min |
| Liver | 24.2 | 27.5 | 22.7 | 22.8 | 21.2 | 23.0 |
| | 16.1–29.3 | 20–29.2 | 20.5–24.2 | 20.1–23.5 | 20.0–24.0 | 21–25 |
| Kidneys | 5.8 | 3.9 | 5.4 | 6.0 | 6.7 | 8.7 |
| | 5.0–6.5 | 3.1–4.5 | 4.2–5.9 | 5.8–6.2 | 6.5–7.0 | 7.5–9.1 |
| Lungs | 4.8 | 6.2 | 7.8 | 4.4 | 3.7 | 2.5 |
| | 4.7–4.9 | 5.7–6.5 | 7.0–8.2 | 4.0–4.8 | 3.2–3.9 | 2.1–3.0 |
| Brain | 0.46 | 0.18 | 0.17 | 0.40 | 0.23 | 0.16 |
| | 0.36–0.59 | 0.15–0.20 | 0.16–0.20 | 0.40–0.40 | 0.21–0.25 | 0.15–0.1 |
| Heart | 2.2 | 0.80 | 0.20 | 1.5 | 0.80 | 0.50 |
| | 1.9–2.5 | 0.6–0.9 | 0.2–0.2 | 1.4–1.7 | 0.75–0.83 | 0.48–0.53 |
| Whole blood | 2.4 | 4.5 | 7.8 | 7.2 | 6.1 | 6.0 |
| | 2.4–2.4 | 4.2–4.9 | 6.8–8.5 | 7.0–7.5 | 5.8–6.9 | 5.7–6.5 |

| | EX. 8 (TCNETMC) $CH_2H_5-O\diagdown N-CS_2 / CH_3$ | | | EX. 9 (TCNETEC) $C_2H_5-O\diagdown N-CS_2 / C_2H_5$ | | |
|---|---|---|---|---|---|---|
| $L_1 = L_2$ whole organs | Time between I.V. injection and sacrifice | | | | | |
| | 5 min | 30 min | 60 min | 5 min | 30 min | 60 min |
| Liver | 18.7 | 22.1 | 29.4 | 21.5 | 29.4 | 28.9 |
| | 17.5–19.1 | 19.5–23.0 | 26.1–32.0 | 16.1–27.2 | 27.5–30.2 | 28.0–29.5 |
| Kidneys | 5.5 | 4.0 | 4.3 | 6.1 | 5.7 | 5.4 |
| | 5.0–5.9 | 3.8–4.3 | 4.0–4.5 | 5.5–7.4 | 5.0–6.0 | 4.9–5.7 |
| Lungs | 5.3 | 9.0 | 6.5 | 4.9 | 2.4 | 1.6 |
| | 5.0–5.8 | 8.4–9.7 | 6.1–6.9 | 4.8–5.1 | 2.1–2.8 | 1.4–1.8 |
| Brain | 0.65 | 0.18 | 0.18 | 0.65 | 0.34 | 0.20 |
| | 0.62–0.69 | 0.15–0.20 | 0.15–0.20 | 0.54–0.75 | 0.30–0.40 | 0.20–0.21 |
| Heart | 1.70 | 0.81 | 0.41 | 2.70 | 2.26 | 1.91 |
| | 1.60–1.80 | 0.80–0.82 | 0.40–0.42 | 2.32–3.08 | 2.1–2.5 | 1.85–2.01 |
| Whole blood | 4.2 | 3.6 | 2.4 | 2.1 | 2.2 | 2.3 |
| | 3.9–4.4 | 3.5–3.7 | 2.3–2.5 | 1.8–3.0 | 2.0–2.2 | 2.0–2.5 |

We claim:

1. A radiopharmaceutical product, comprising a complex of a transition metal having the formula:

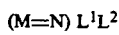

in which M is a transition metal and L¹ and L², which can be the same or different, have the formula:

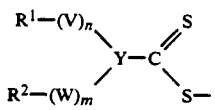

in which V and W, which can be the same or different, represent O, S or Se, n and m, which can be the same or different, are equal to 0 or to 1, Y represents N, P or As, and R¹ and R², which can be the same or different, represent a straight or branched alkyl radial with 1 to 10 carbon atoms, which is either not substituted or substituted by —O—R³, OOC—R³, OCNR⁴R⁵ or —NR⁴R⁵ groups, in which R³ is a straight or branched alkyl radical with 1 to 5 carbon atoms and R⁴ and R⁵, which can be the same or different, are hydrogen atoms or straight or branched alkyl radicals with 1 to 5 carbon atoms, or in which R¹ and R² together form a hydrocarbon ring optionally containing one or more heteroatoms, wherein R¹ and R² are not both unsubstituted alkyl radicals when n and m are equal to 0.

2. Radiopharmaceutical product according to claim 1, characterized in that M represents a rhenium or technetium isotope.

3. Radiopharmaceutical product according to claim 2, characterized in that the technetium isotope is Tc 99 m.

4. Radiopharmaceutical product according to claim 2, characterized in that the rhenium isotope is Re-186 or Re-188.

5. Radiopharmaceutical product according to any one of the claims 1 to 4, characterized in that Y represents N, m and n are equal to 0 and L¹ and L² are identical.

6. Radiopharmaceutical product according to claim 5, characterized in that R¹ and R² represent unsubstituted alkyl radicals.

7. Radiopharmaceutical product according to claim 5, characterized in that at least one of the R¹ and R² is an alkoxyalkyl radical.

8. Radiopharmaceutical product according to claim 7, characterized in that R¹ represents CH₃O—CH₂—CH₂— and R² represents CH₃—CH₂— or CH₃OCH₂—CH₂—.

9. Radiopharmaceutical product according to claim 7, characterized in that R¹ represents CH₃—CH₂— and R² represents CH₃—O—CH₂—CH₂—CH₂— or C₂H₅—O—CH₂—CH₂.

10. Radiopharmaceutical product according to any one of the claims 1 to 4, wherein Y represents N and L¹ and L² have the formula:

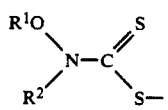

in which R¹ and R², which can be the same or different, represent a straight or branched alkyl radical with 1 to 10 carbon atoms, which is either not substituted or substituted by —O—R³, OOC—R³, OCNR⁴R⁵ or —NR⁴R⁵ groups, in which R³ is a straight or branched alkyl radical with 1 to 5 carbon atoms and R⁴ and R⁵, which can be the same or different, are hydrogen atoms or straight or branched alkyl radicals with 1 to 5 carbon atoms, or in which R¹ and R² together form a hydrocarbon ring optionally containing one or more heteroatoms.

11. Radiopharmaceutical product according to claim 10, characterized in that R¹ represents CH₃— and R² represents CH₃— or CH₃—CH₂—.

12. Radiopharmaceutical product according to claim 10, characterized in that R¹ represents CH₃—CH₂— and R² represents CH₃— or CH₃—CH₂—.

13. A process for the preparation of a radiopharmaceutical product according to Claim 1, said process comprising the following successive steps:
reacting an oxygenated compound of a titanium metal M with:
a) a first ligand selected from the group consisting of substituted or unsubstituted, aromatic and aliphatic phosphines and polyphosphines and
b) a second reagent selected from the group consisting of ammonium and alkali metal nitrides and the nitrogenous ligands having a >N—N< in which the N are connected to hydrogen atoms and/or to monovalent organic groups via a carbon atom, or in which one of the N is connected to the carbon atom of a divalent organic group via a double bond and the other N is connected to hydrogen atoms and/or monovalent organic groups via a carbon atom and
reacting the intermediate obtained in the first step with a compound having the formula:

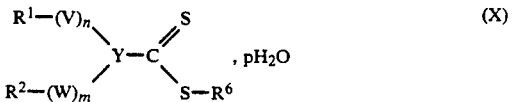

in which V and W, which can be same or different, represent O, S or Se, n and m, which can be the same or different, are equal to 0 or to 1, Y represents N, P or As, and R¹ and R², which can be the same or different, represent a straight or branched alkyl radical with 1 to 10 carbon atoms, which is either not substituted or substituted by —O—R³, OOC—R³, OCNR⁴R⁵ or —NR⁴R⁵ groups, in which R³ is a straight or branched alkyl radical with 1 to 5 carbon atoms and R⁴ and R⁵, which can be the same or different, are hydrogen atoms or straight or branched alkyl radicals with 1 to 5 carbon atoms, or in which R¹ and R² together form a hydrocarbon ring optionally containing 1 or more heteroatoms, R⁶ is an alkali metal ion, H⁺ or NH₄⁺ and p is equal to 0 or an integer between 1 and 5.

14. Process according to claim 13, characterized in that the oxygenated compound of the transition metal is an ammonium or alkali metal pertechnetate.

15. Process according to claim 13, characterized in that the oxygenated compound of the transition metal is ammonium or alkali metal perrhenate.

16. Process according to claim 13, characterized in that the first ligand is a phosphine chosen from among triphenyl phosphine, diethyl phenyl phosphine, triethyl phosphine, trimethyl phosphine, tris(2-cyanoethyl)-phosphine and trisulphonated triphenyl phosphine.

17. Process according to claim 13, characterized in that the second reagent is chosen from among S-methyl-dithiocarbazate, S-methyl-N-methyldithiocarbazate, alpha-N-methyl-S-methyl beta-N-pyridylmethylene dithiocarbazate, S-methyl-beta-N-(2-hydroxyphenyl)-methylene dithiocarbazate and alpha-N-methyl-S-methyl-beta-N-(2-hydroxyphenyl)methylene dithiocarbazate.

18. Process according to claim 13, characterized in that the second reagent is sodium nitride.

19. A kit for the preparation of a radiopharmaceutical product, comprising a first bottle containing a phosphine, a second bottle containing sodium nitride, dithiocarbazic acid or a derivative thereof and a third bottle containing a compound having the formula:

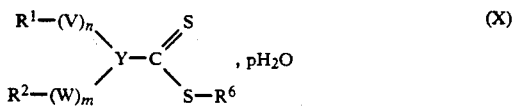 (X)

in which V and W, which can be same or different, represent O, S or Se, n and m, which can be the same or different, are equal to 0 or to 1, Y represents N, P or As, and $R^1$ and $R^2$, which can be the same or different, represent a straight or branched alkyl radical with 1 to 10 carbon atoms, which is either not substituted or substituted by $-O-R^3$, $OOC-R^3$, $OCNR^4R^5$ or $-NR^4R^5$ groups, in which $R^3$ is a straight or branched alkyl radical with 1 to 5 carbon atoms and $R^4$ and $R^5$, which can be the same or different, are hydrogen atoms or straight or branched alkyl radicals with 1 to 5 carbon atoms, or in which $R^1$ and $R^2$ together form a hydrocarbon ring optionally containing 1 or more heteroatoms, $R^6$ is an alkali metal ion, $H^+$ or $NH_4^+$ and p is equal to 0 or an integer between 1 and 5.

20. A method of diagnosis or therapy for heart conditions, comprising administering to a patient in need thereof an effective amount of a radiopharmaceutical product comprising a complex of a transition metal having the formula:

$(M\equiv N) L^1 L^2$ in which M is a transition metal and $L^1$ and $L^2$, which can be the same or different, have the formula:

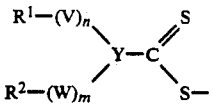 (II)

in which V and W, which can be the same or different, represent O, S or Se, n and m, which can be the same or different, are equal to 0 or to 1, Y represents N, P or As, and $R^1$ and $R^2$, which can be the same or different, represent a straight or branched alkyl radial with 1 to 10 carbon atoms, which is either not substituted or substituted by $-O-R^3$, $OOC-R^3$, $OCNR^4R^5$ or $-NR^4R^5$ groups, in which $R^3$ is a straight or branched alkyl radical with 1 to 5 carbon atoms and $R^4$ and $R^5$, which can be the same or different, are hydrogen atoms or straight or branched alkyl radicals with 1 to 5 carbon atoms, or in which $R^1$ and $R^2$ together form a hydrocarbon ring optionally containing one or more heteroatoms.

21. The method of claim 20, wherein said method of diagnosis is myocardial scintigraphy.

22. A method of diagnosis or therapy for heart conditions, comprising administering to a patient in need thereof an effective amount of a radiopharmaceutical product comprising a complex of a transition metal having the formula:

$(M\equiv N) L^1 L^2$ in which M is a transition metal and $L^1$ and $L^2$, which can be the same or different, have the formula:

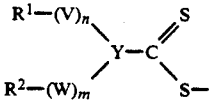 (II)

in which V and W, which can be the same or different, represent O, S or Se, n and m, which can be the same or different, are equal to 0 or to 1, Y represents N, P or As, and $R^1$ and $R^2$, which can be the same or different, represent a straight or branched alkyl radial with 1 to 10 carbon atoms, which is either not substituted or substituted by $-O-R^3$, $OOC-R^3$, $OCNR^4R^5$ or $-NR^4R^5$ groups, in which $R^3$ is a straight or branched alkyl radical with 1 to 5 carbon atoms and $R^4$ and $R^5$, which can be the same or different, are hydrogen atoms or straight or branched alkyl radicals with 1 to 5 carbon atoms, or in which $R^1$ and $R^2$ together form a hydrocarbon ring optionally containing one or more heteroatoms, wherein $R^1$ and $R^2$ are not both unsubstituted alkyl radicals when n and m are equal to 0.

23. The method of claim 22, wherein said method of diagnosis is miocardia scintigraphy.

* * * * *

UNITED STATES PATENT AND TRADEMARK OFFICE
CERTIFICATE OF CORRECTION

PATENT NO.   : 5,288,476
DATED        : February 22, 1994
INVENTOR(S)  : Roberto PASQUALINI, et al.

It is certified that error appears in the above-indentified patent and that said Letters Patent is hereby corrected as shown below:

On the title page, Item [75], the inventorship and, Item [30], the 2nd Foreign Application Priority Data should read as follows:

[75]--Roberto Pasqualini, Clamart, France; Luciano Magon, Padova, Italy; André Bardy, Morangis, France; Adriano Duatti, Chiesuol Fosso, Italy; Andrea Marchi, Ferrara, Italy--

[30]--Nov. 25, 1988 [FR]  France ............. 88 15415--

Signed and Sealed this

Twenty-first Day of June, 1994

Attest:

BRUCE LEHMAN

*Attesting Officer*    Commissioner of Patents and Trademarks